United States Patent
Lee et al.

(10) Patent No.: US 10,413,725 B2
(45) Date of Patent: Sep. 17, 2019

(54) ELECTRICAL STIMULATION DEVICE

(71) Applicant: y-Brain Inc, Daejeon (KR)

(72) Inventors: Ki Won Lee, Seongnam-si (KR); Cheon Ju Ko, Yongin-si (KR); Jong Min Jang, Suwon-si (KR); Byung Gik Kim, Daegu (KR)

(73) Assignee: Y-BRAIN INC., Daejeon (KR)

( * ) Notice: Subject to any disclaimer, the term of this patent is extended or adjusted under 35 U.S.C. 154(b) by 2 days.

(21) Appl. No.: 15/235,080

(22) Filed: Aug. 11, 2016

(65) Prior Publication Data

US 2018/0043152 A1 Feb. 15, 2018

(51) Int. Cl.
*A61N 1/04* (2006.01)
*A61N 1/08* (2006.01)
*A61N 1/36* (2006.01)
*A61N 1/20* (2006.01)

(52) U.S. Cl.
CPC ....... *A61N 1/3603* (2017.08); *A61N 1/36025* (2013.01); *A61N 1/0456* (2013.01); *A61N 1/0476* (2013.01); *A61N 1/0484* (2013.01); *A61N 1/0492* (2013.01); *A61N 1/205* (2013.01)

(58) Field of Classification Search
None
See application file for complete search history.

(56) References Cited

U.S. PATENT DOCUMENTS

2008/0306567 A1* 12/2008 Park .................. A61N 1/36185 607/27
2009/0187223 A1* 7/2009 Gross .................. A61F 7/12 607/3
2012/0109230 A1* 5/2012 Kothandaraman .................. A61N 1/37247 607/2
2013/0110220 A1* 5/2013 Brown ................ A61N 1/0484 607/149
2014/0257448 A1* 9/2014 Arle .................... A61N 1/0484 607/139
2015/0238759 A1* 8/2015 Katsnelson ........ A61N 1/36025 607/66
2016/0310730 A1* 10/2016 Martins ................ A61N 1/3601
2018/0146898 A1* 5/2018 Begtrup ............... G01N 33/487

FOREIGN PATENT DOCUMENTS

JP  3129187      1/2007
JP  2009530064 A 8/2009
KR  200427527 B1 9/2006

OTHER PUBLICATIONS

Korean Office Action dated Jul. 29, 2015 corresponding to Korean Application No. 10-2015-0054419 citing the above reference(s).

* cited by examiner

*Primary Examiner* — Erica S Lee
(74) *Attorney, Agent, or Firm* — Studebaker & Brackett PC

(57) ABSTRACT

Provided is an electrical stimulation device. The electrical stimulation device includes a first electrode that contacts a first portion of the head of a user to apply a current to the head of the user, a second electrode that contacts a second portion that is different from the first portion of the head of the user to apply a current to the head of the user, a controller that performs a control such that polarities of the first electrode and the second electrode can be changed based on a reference comprising at least one of a reference time, a reference pH index, and a reference number of uses.

14 Claims, 5 Drawing Sheets

ELECTRICAL STIMULATION DEVICE

BACKGROUND

The inventive concept relates to an electrical stimulation device for applying an electrical stimulus to the head of the user.

Meanwhile, a brain electrical stimulation technology using a transcranial direct current stimulation (tDCS) is known to be effective to improve a recognition ability and treat mental diseases such as depression or attention deficit hyperactivity disorders (ADHD).

Accordingly, if the bran electrical stimulation technology may be used in everyday lives, the brain function may be improved, and mental diseases may be continuously treated by activating or retraining connections between nerves.

A tDCS device according to the related art includes a plurality of electrodes, and each of the electrodes includes a patch layer that contacts skin of the head of the user and an electrode layer that transfers a current to the patch layer. The patch layer contains an electrolyte for flows of currents, and thus an oxidation/reduction reaction may occur on an interface between the patch layer and the electrode layer. The oxidation/reduction reaction gradually acidifies or basifies the patch layer, and if the pH index of the patch layer deviates from a threshold range, the skin of the head of the user, which contacts the patch layer, may be burned.

SUMMARY

Accordingly, the inventive concept has been made in an effort to solve the above-mentioned problems, and provides an electrical stimulation device that may prevent skin of the head of the user from being burned when the user uses the electrical stimulation device.

In accordance with an aspect of the inventive concept, there is provided an electrical stimulation device including a first electrode that contacts a first portion of the head of a user to apply a current to the head of the user, a second electrode that contacts a second portion that is different from the first portion of the head of the user to apply a current to the head of the user, a controller that performs a control such that the first electrode has a first polarity and the second electrode has a second polarity that is opposite to the first polarity at a first time point and such that the first electrode has the second polarity and the second electrode has the first polarity at a second time point that is different from the first time point, based on a reference, and an indicator that indicates polarity states of the first electrode and the second electrode, wherein the reference comprises at least one of a reference time, a reference pH index, and a reference number of uses.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, an electrical stimulation device according to embodiments of the inventive concept will be described with reference to the accompanying drawings.

"Electrical stimulation" that will be mentioned in the following may refer to transcranial current stimulation (tCS) such as transcranial direct current stimulation (tDCS), transcranial alternating current stimulation (tACS), and transcranial random-noise stimulation, but the inventive concept is not limited thereto.

Figure 1:
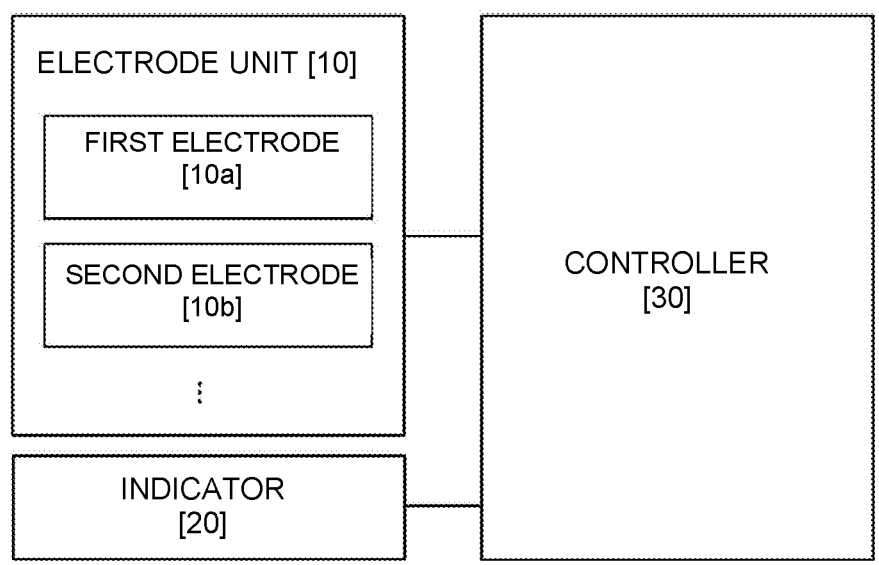
FIG. 1 is a block diagram illustrating a schematic configuration of an electrical stimulation device according to an embodiment of the inventive concept.
Figure 2:
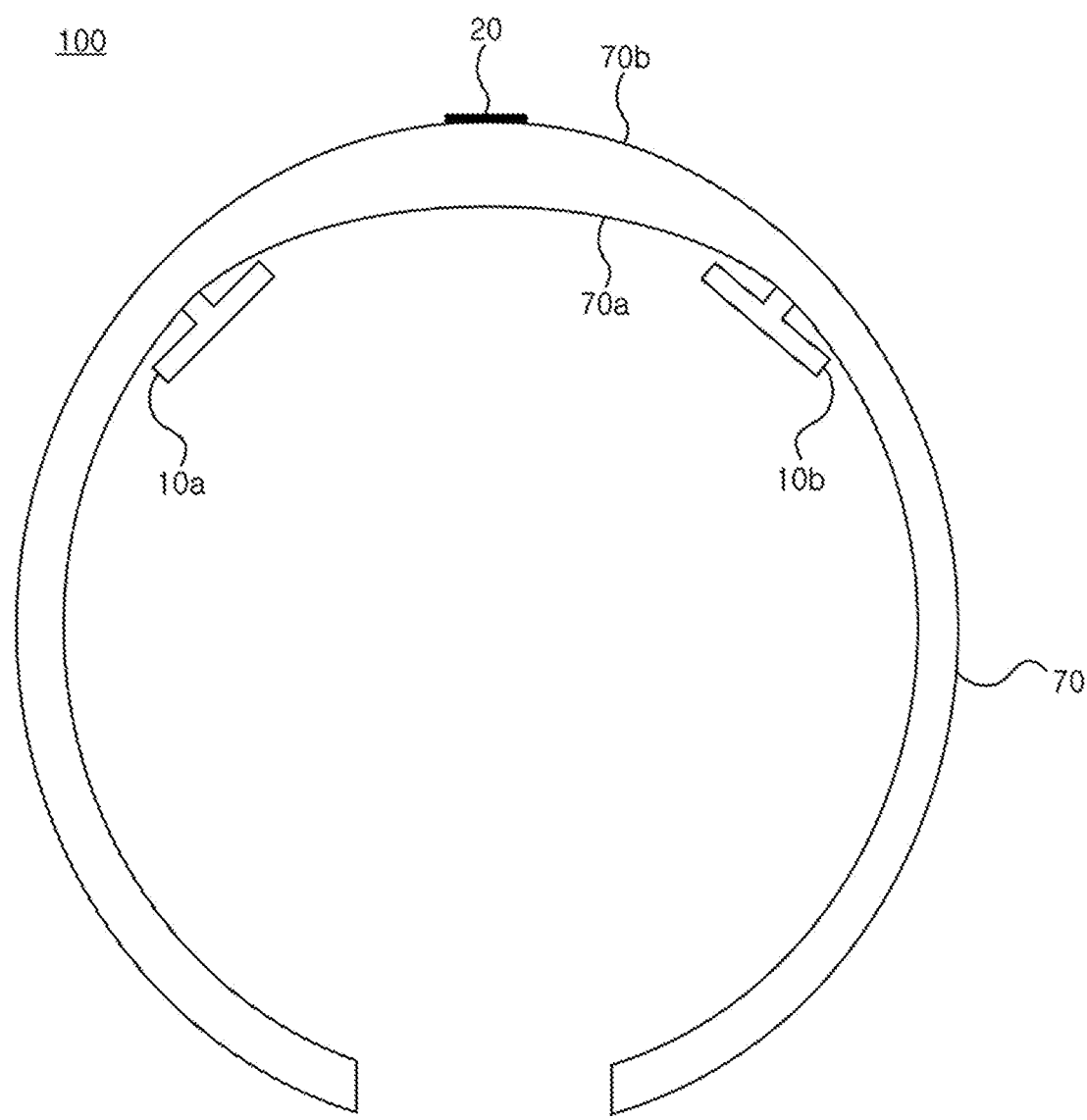
FIG. 2 is a view illustrating a schematic external appearance of the electrical stimulation device according to the embodiment of the inventive concept.

FIG. 1 is a block diagram illustrating a schematic configuration of an electrical stimulation device according to an embodiment of the inventive concept. FIG. 2 is a view illustrating a schematic external appearance of the electrical stimulation device according to the embodiment of the inventive concept.

Referring to FIG. 1, the electrical stimulation device 100 according to the embodiment of the inventive concept includes an electrode unit 10, an indicator 20, and a controller 30.

The electrode unit 10 contacts the head of the user (a target object) and applies a current to the head of the user. The user may mount the electrical stimulation device 100 on the head or may attach the electrical stimulation device 100 to the head, and thus the electrode unit 10 may contact the head of the user. For example, the electrode unit 10 may contact the forehead of the user, but the inventive concept is not limited thereto.

A plurality of electrode units 10 (a first electrode 10a and a second electrode 10b) may be provided. The electrical stimulation device 100 may apply currents to a plurality of portions of the head of the user. For example, one electrode unit 10 (for example, the first electrode 10a) may be situated adjacent to the left side of the head of the user to contact the left side of the head, and another electrode 10 (the second electrode 10b) may be situated adjacent to the right side of the head of the user to contact the right side of the head. A plurality of electrode units 10 may be controlled independently.

The electrodes 10 have polarities as described below. The electrode units 10 may be controlled to have different polarities. However, the inventive concept is not limited thereto, but some electrode units 10 may have the same polarity depending on the number of the electrode units 10.

The indicator 20 indicates polarity states of the plurality of electrode units 10. Here, "indication" may include a series of operations of directly clarifying or expressing or indirectly hinting polarity states of the plurality of electrode units 10, or sending signals such that the user may recognize the polarity states of the plurality of electrode units 10.

As an example, the indicator 20 may include light emitting elements that are turned on and off or emit different light colors depending on the polarity states of the first electrode 10a and the second electrode 10b. One or a plurality of electrode units 10 may be provided depending on the number of the electrode units 10.

As another example, the indicator 20 may include a speaker that outputs a specific sound depending on the polarity states of the first electrode 10a and the second electrode 10b. The speaker may be used to output guide information related to the mounting of the electrical stimulation device 100.

As another example, the indicator 20 may include a display that displays a letter, a number, a figure, an image, or the like depending on the polarity states of the first electrode 10a and the second electrode 10b.

The polarity states of the plurality of electrode units 10 may correspond to the mounting direction of the electrical stimulation device 100. This point may be particularly important when the shape of the electrical stimulation device 100 is (vertically or horizontally) symmetrical. According to an embodiment, there may be an occasion in which a flow of a current on the head of the user has to be fixed in a specific direction to allow the electrical stimulation device 100 to perform some functions or increase the effects of some functions. In this case, because the polarity states of the plurality of electrode units 10 are related to the flows of currents, it is necessary to guide the mounting direction of the electrical stimulation device 100 to the user by the electrical stimulation device 100. Accordingly, the user may recognize the mounting direction of the electrical stimulation device 100 from the indication of the indicator 20.

According to an embodiment, the electrical stimulation device 100 may include a tDCS device that is configured such that the shape of a frame having electrodes on the left and right sides thereof is symmetrical. The user may wear the electrical stimulation device 100 after determining the left and right sides through a random selection. In this case, the controller 30 may detect a direction in which the user wears the electrical stimulation device 100, and may apply a current to the head of the user by controlling the electrode unit 10 such that the electrode unit 10 corresponds to the mounting direction of the electrical stimulation device 10.

The controller 30 generally controls functions and operations of the electrical stimulation device 100. The controller 30 may control the electrode unit 10 such that a current is applied to the head of the user. The controller 30 may control the indicator 20 such that the polarity states of the electrode unit 10 are indicated to the user. The controller 30 may include a processor, a microprocessor, a micro controller, a central processing unit (CPU), a micro processing unit (MPU), and a micro controller unit (MCU).

Meanwhile, the elements of FIG. 1 are not essential to the electrical stimulation device 100 according to the embodiment of the inventive concept, and thus the electrical stimulation device 100 may include more or less elements.

Referring to FIG. 2, the electrical stimulation device 100 according to the embodiment of the inventive concept includes a frame 70, an electrode unit 10, and an indicator 20.

The electronic unit 10 may be arranged on a first surface 70a of the frame 70, and the indicator 20 may be arranged on a second surface 70b of the frame 70. The first surface 70a may be an inner surface of the frame 70, and the second surface 70b may be an outer surface of the frame 70. When the electrical stimulation device 100 is mounted on or attached to the head of the user, the first surface contacts the head of the user.

As described above, a plurality of electrode units 10 (a first electrode 10a and a second electrode 10b) may be provided. Each of the plurality of electrode units 10 may include a patch layer 12 and an electrode layer 11.

The patch layer 12 is a layer that directly contacts skin of the head of the user. The patch layer 12 may include a single layer. The patch layer 12 applies a current transferred from the electrode layer 11 to the head of the user. To achieve this, the patch layer 12 may include an electrolyte for transferring a current. For example, the patch layer 12 may include sponge or hydrogel that contains an electrolyte, but the inventive concept is not limited thereto. The electrolyte may include chlorine ions (CL) that are commonly present in skin of the user. The patch layer 12 may be formed of a material having a relatively high impedance.

The electrode layer 11 is formed on the patch layer 12. The electrode layer 11 does not directly contact skin of the head of the user. As described above, the electrode layer 11 transfers a current to the patch layer 12 to apply an electrical stimulus to the user through the patch layer 12. For example, the electrode layer 11 may include a conductive carbon sheet or conductive silicon, but the inventive concept is not limited thereto.

Figure 3:
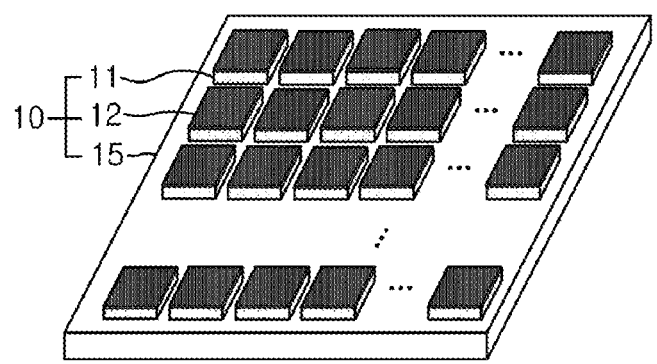
FIG. 3 is a view illustrating a configuration of an electrode unit.

As illustrated in FIG. 3, the electrode unit 10 may include a plurality of segments, and the plurality of segments may be formed on the circuit board 15 to be spaced apart from each other. Each of the segments may include a patch layer 12 and an electrode layer 11. The number, shapes, intervals of the segments may be variously modified according to embodiments. The plurality of segments may be independently controlled by the controller 30. Further, some segments may constitute a group to be controlled by the controller 30. As illustrated in FIG. 3, the electrode unit 10 may not be divided into a plurality of segments.

As described above, the indicator 20 indicates the polarity states of the plurality of electrode units 10. The arrangement location of the indicator 20 on the second surface may be variously modified according to embodiments.

Meanwhile, the whole shape of the electrical stimulation device 100 is not limited to the embodiment of FIG. 1.

Figure 4:
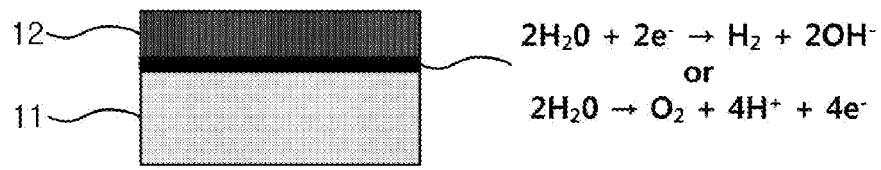
FIG. 4 is a view for explaining a water splitting reaction on an interface between a patch layer and an electrode layer.

FIG. 4 is a view for explaining a water splitting reaction on an interface between a patch layer and an electrode layer.

Referring to FIG. 4, a water splitting reaction occurs on an interface between the patch layer 12 and the electrode layer 11 when a current is transferred from the electrode layer 11 to the patch layer 12. The patch layer 12 may include water (used as a solvent) in addition to the electrolyte, and the water of the patch layer 12 reacts electrons provided by the electrode layer 11 to be split into hydroxide ions (OH+) and hydrogen molecules. Further, the water of the patch layer 12 may lose electrons to be split into hydrogen ions (H+) and oxygen molecules. Accordingly, when the electrode unit 10 functions as a cathode, the pH index of the patch layer 12 of the electrode unit 10 may be gradually increased by the hydroxide ions, and similarly, when the electrode unit 10 functions as an anode, the pH index of the patch layer 12 of the electrode unit 10 may be gradually decreased by the hydrogen ions. Further, the change of the pH index of the patch layer 12 deviates a threshold range, the skin of the head of the user, which contacts the patch layer 12 may be burned.

Figure 5:
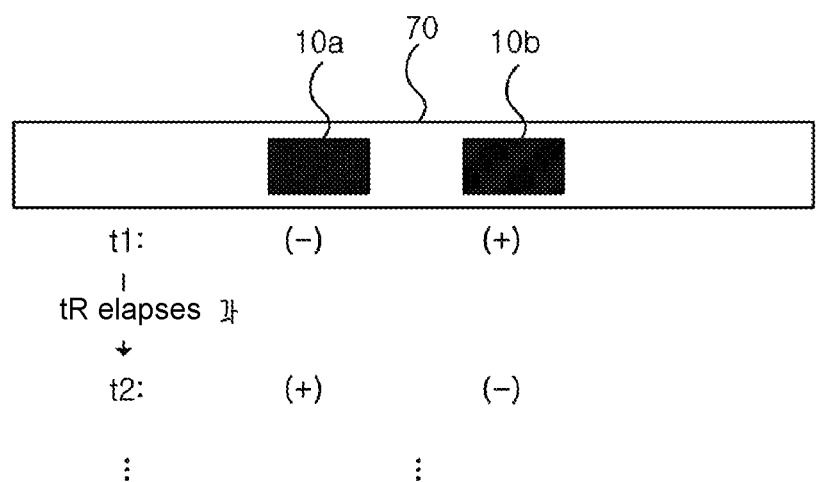
FIG. 5 is a view for explaining periodical changes of polarities of a first electrode and a second electrode.

FIG. 5 is a view for explaining periodical changes of polarities of a first electrode and a second electrode.

Referring to FIG. 5, a control is made such that the first electrode 10a has a first polarity (for example, a cathode (−)) and the second electrode 10b has a second polarity (for example, an anode (+)) at a first time point t1. Thereafter, a control is made such that the first electrode 10a has the second polarity and the second electrode 10b has the first polarity at a second time point t2 that is a predetermined reference time period (tR) after the first time point t1. The reference time may be set in unit of hours, minutes, or seconds. The hydroxide ions generated by the first electrode 10a or the hydrogen ions generated by the second electrode 10b through the water splitting reaction at the first time point returns to water through a reverse reaction at the second time point. The polarities of the plurality of electrodes may continue to change while the reference time period is a period of the change.

According to embodiments, the polarities of the plurality of electrodes may be changed depending on a reference pH index and the reference number of uses. To achieve this, the electrical stimulation device 100 may further include a pH sensor (not illustrated) for measuring a pH index of the patch layer 12. The pH sensor may be arranged in the electrode unit 10. An excess of the reference number of uses may be determined based on a time period for one-time use or the number of power on-and-offs.

Accordingly, the pH index of the patch layer 12 may be maintained within a safety range, and consequently, the skin of the head the user, which contacts the patch layer 12 can be prevented from being burned.

The inventive concept has the following effects.

First, the polarities of the plurality of electrodes are periodically changed based on a reference, the pH index of the patch layer can be maintained in a safety range so that skin of the head of the user, which contacts the patch layer, can be prevented from being burned.

For example, in the tDCS device including two electrodes, only an oxidation reaction continuously occurs in one electrode and only a reduction reaction occurs in the other electrode so that the patch layers are easily acidified or basified.

The inventive concept provides a configuration in which a tDCS device is formed such that the shape of the frame having electrodes on the left and right sides thereof are symmetrical and the indicator for indicating a mounting direction of the tDCS device to the user is provided. Then, the indicator can indicate a (left and right) mounting direction of the tDCS device for every set period, and accordingly, can solve a conventional problem in which a specific chemical reaction is made only for a specific electrode.

According to an embodiment of the inventive concept, an effect of increasing an in-use time of the electrode and preventing burning of the user can be provided by preventing a problem in which a specific reaction is made only for a specific electrode of the tDCS device.

Second, the user can wear the electrical stimulation device such that the left and right sides of the electrical stimulation device is correct. In the first embodiment, the user can easily recognize the mounting direction of the electrical stimulation device corresponding to the polarities of the plurality of electrodes as the polarity states of the plurality of electrodes of the electrical stimulation device are indicated. Accordingly, the user may wear the electrical stimulation device correctly.

In the second embodiment, the tDCS device is constituted such that the shape of the frame having electrodes on the left and right sides thereof is symmetrical, and thus electrical signals suitable for the electrodes can be applied to correspond to the mounting state if the user wears the tDCS device. If the tDCS device, of which the left and right sides cannot be distinguished, is provided and the left and right sides of the tDCS device is determined through a random selection of the user, an electrical signal is applied to correspond to the determination and thus the tDCS device can be conveniently used while the user does not consider the left and right sides of the tCDS device. Further, the inventive concept can solve a conventional problem in which a specific chemical reaction is made only for a specific electrode.

Although the embodiments of the electrical stimulation devices 100 that apply an electrical stimulus to the head of the user have been described in the specification, the technical features of the inventive concept also may be applied to the electrical stimulation device 100 for applying an electrical stimulus to another body portion of the user in addition to the head of the user in substantially the same manner.

What is claimed is:
1. An electrical stimulation device comprising:
a plurality of electrode units formed on a circuit board to be spaced apart from each other, wherein the plurality of electrodes comprising:
a first electrode configured to
contact a first portion of a head of a user, and
supply a current to the head of the user; and
a second electrode configured to
contact a second portion that is different from the first portion of the head of the user, and
supply a current to the head of the user;
a controller connected to the plurality of electrode units, and configured to, based on a predetermined reference,
control the first electrode to supply a first current having a first polarity and the second electrode to supply a second current having a second polarity that is opposite to the first polarity at a first time point, and
control the first electrode to supply the second current having the second polarity and the second electrode to supply the first current having the first polarity at a second time point that is different from the first time point; and
an indicator connected to the controller, and configured to indicate polarity states of the first electrode and the second electrode,
wherein each of the first electrode and the second electrode comprises
a patch layer having an electrolyte and configured to contact skin of the head of the user,
an electrode layer formed on the patch layer to transfer at least one of the first current and the second current to the patch layer, and
a potential of hydrogen (pH) sensor configured to measure a pH index of the patch layer,
wherein the predetermined reference comprises at least one of a reference time, a reference pH index, and a reference number of uses, and
wherein the controller is configured to change the first polarity of the first electrode based on the measured pH index of the patch layer of the first electrode, and change the second polarity of the second electrode based on the measured pH index of the patch layer of the second electrode, and
wherein the controller configured to
detect a mounting direction in which the user wears the electrical stimulation device, and
change each of the first polarity of the first electrode and the second polarity of the second electrode when it is detected that the detected mounting direction in which the user wears the electrical stimulation device is opposite to a predetermined mounting direction.
2. The electrical stimulation device of claim 1, wherein the indicator comprises at least one light emitting element that is turned on and off or emit different light colors depending on the polarity states of the first electrode and the second electrode.

3. The electrical stimulation device of claim 1, wherein the indicator comprises at least one speaker that outputs a predetermined sound depending on the polarity states of the first electrode and the second electrode.

4. The electrical stimulation device of claim 1, wherein the indicator displays at least one of a letter, a number, a figure, and an image depending on the polarity states of the first electrode and the second electrode.

5. The electrical stimulation device of claim 1, further comprising:
a frame having a first surface on which the first electrode and the second electrode are arranged and a second surface that is different from the first surface, on which the indicator is arranged.

6. The electrical stimulation device of claim 5, wherein each of the first electrode and the second electrode has a T-shape protruded from the first surface.

7. The electrical stimulation device of claim 1, wherein a water splitting reaction occurs on an interface between the patch layer and the electrode layer when a current is transferred to the patch layer.

8. The electrical stimulation device of claim 1, wherein the patch layer is sponge or hydrogel that contains an electrolyte.

9. The electrical stimulation device of claim 1, wherein the pH sensor is configured to periodically measure the pH index of the patch layer, and the controller configured to periodically change the first polarity and the second polarity, respectively, based on the periodically measured pH index.

10. An electrical stimulation device comprising:
a first electrode configured to
contact a first portion of a head of a user, and
supply a current to the head of the user;
a second electrode configured to
contact a second portion that is different from the first portion of the head of the user, and
supply a current to the head of the user; and
a controller configured to
control the first electrode to supply a first current having a first polarity and the second electrode to supply a second current having a second polarity that is opposite to the first polarity at a first time point, and
control the first electrode to supply the second current having the second polarity and the second electrode to supply the first current having the first polarity at a second time point that is different from the first time point,
wherein each of the first electrode and the second electrode comprises
a patch layer having an electrolyte and configured to contact skin of the head of the user,
an electrode layer formed on the patch layer to transfer at least one of the first current and the second current to the patch layer, and
a potential of hydrogen (pH) sensor configured to measure a pH index of the patch layer, and
wherein the controller is configured to change the first polarity of the first electrode based on the measured pH index of the patch layer of the first electrode, and change the second polarity of the second electrode based on the measured pH index of the patch layer of the second electrode.

11. The electrical stimulation device of claim 10, further comprising:
an indicator connected to the control, and configured to indicate polarity states of the first electrode and the second electrode.

12. The electrical stimulation device of claim 11, wherein each of the first electrode and the second electrode has a T-shape protruded from a first surface of a frame having the first surface on which the first electrode and the second electrode are arranged and a second surface that is different from the first surface, on which the indicator is arranged.

13. The electrical stimulation device of claim 10, wherein the controller configured to
detect a mounting direction in which the user wears the electrical stimulation device, and
change each of the first polarity of the first electrode and the second polarity of the second electrode when it is detected that the detected mounting direction in which the user wears the electrical stimulation device is opposite to a predetermined mounting direction.

14. The electrical stimulation device of claim 10, wherein the pH sensor is configured to periodically measure the pH index of the patch layer, and the controller configured to periodically change the first polarity and the second polarity, respectively, based on the periodically measured pH index.

* * * * *